(12) United States Patent
Browne

(10) Patent No.: US 9,320,542 B2
(45) Date of Patent: Apr. 26, 2016

(54) DEVICE FOR TREATING FLAIL CHEST

(71) Applicant: Graeme A. Browne, Prior Lake, MN (US)

(72) Inventor: Graeme A. Browne, Prior Lake, MN (US)

(*) Notice: Subject to any disclaimer, the term of this patent is extended or adjusted under 35 U.S.C. 154(b) by 38 days.

(21) Appl. No.: 14/077,596

(22) Filed: Nov. 12, 2013

(65) Prior Publication Data

US 2014/0214032 A1   Jul. 31, 2014

Related U.S. Application Data

(60) Provisional application No. 61/725,116, filed on Nov. 12, 2012.

(51) Int. Cl.
*A61B 17/00* (2006.01)
*A61F 4/00* (2006.01)
*A61F 5/04* (2006.01)
*A61B 17/64* (2006.01)

(52) U.S. Cl.
CPC .................................. *A61B 17/6433* (2013.01)

(58) Field of Classification Search
CPC ........ A61B 17/60; A61B 17/66; A61B 17/70; A61B 17/7056
USPC ................. 606/246–249, 250–253, 264–278; 600/201–246
See application file for complete search history.

(56) References Cited

U.S. PATENT DOCUMENTS

| | | | |
|---|---|---|---|
| 4,611,582 A * | 9/1986 | Duff .................... | A61B 17/7047 606/258 |
| 8,790,380 B2 * | 7/2014 | Buttermann ......... | A61B 17/707 606/324 |
| 2004/0225289 A1 * | 11/2004 | Biedermann et al. ........... | 606/61 |
| 2011/0098757 A1 * | 4/2011 | Schelling ........... | A61B 17/7079 606/324 |

* cited by examiner

*Primary Examiner* — Ellen C Hammond
*Assistant Examiner* — Christina Negrellirodriguez
(74) *Attorney, Agent, or Firm* — Beck Tysver Evans PLLC; Robert Beck

(57) ABSTRACT

A flail chest stabilizing device to permit transportation of injured patients that finds effective use in battlefield and emergency medical settings.

1 Claim, 3 Drawing Sheets

DEVICE FOR TREATING FLAIL CHEST

CROSS-REFERENCE TO RELATED CASES

The present case is the utility conversion of U.S. Provisional Application 61/725,116, filed Nov. 12, 2012, which is incorporated by reference in its entirety.

BACKGROUND OF THE INVENTION

Flail chest is a medical condition that occurs when several ribs are broken in several places. The injury destroys the integrity of the chest cavity and consequently it can no longer support respiration. Acute treatment options include mechanical ventilation (intubation) which does not require an intact chest. In former times and in a hospital setting a system of weights would be set up bedside. Each rib would have been attached to weight that was draped over a pulley system to allow the ribs to re-approximate their positions under the pull of gravity on the weights. This technique supplies sufficient rigidity to support respiration but has been abandoned in clinical practice.

Today flail chest is a common battlefield injury where protective body armor distributes mechanical stresses over the entire chest. If enough force is applied many ribs will break in many locations at once. The injury is also common in high-speed automobile crashes where the steering wheel can cause a blunt trauma to the chest.

The device and system of the present invention maybe used in a field setting or hospital setting and may be very useful for transporting the injured in a vehicle where weight systems and respirators are unworkable.

SUMMARY OF THE INVENTION

The device of the invention is a system with several integral and several optional components. At a minimum the system includes one rib clamps for attachment to a flail (broken) rib, and a close by rib clamp connected to a more intact rib, in essentially every instance three or more rib clamps will likely be deployed. Each rib clamp has a terminal pin or proximal cap that carries a groove to accept an O-ring. All the rib clamps protrude though and resiliently and flexibly connect to an elongate connector bar. The connector bar has several (usually three) multiple pin or cap reception holes. In use the rib clamps support the ribs and the connector bar supports the rib clamps. Together they cooperate to re-approximate correct rib position and support the chest cavity sufficiently to support respiration.

In general each rib clamp has distal tips shaped to grasp a curved rib surface. These distal tips are passed through the chest wall and can be fixed onto intact sections of broken ribs and onto adjacent intact ribs. Each clamp is screw adjustable onto the rib, and has a shank that terminates in a proximal pin or cap. Each pin or cap extends beyond the surface of the patient's chest. A connector bar forms a support strap that interconnects the several pins or caps and distributes the forces over much of the chest area. In use each rib clamp is affixed to rib segment and pulled into approximate position reestablishing the morphology of the chest cavity, this process is facilitated by the presence of complementary clamps on adjacent ribs.

Next the connector bar support straps are arranged to pick up the pins and affix them to the support strap. Typically the interconnection of injured ribs to each other and to one or more intact ribs is sufficient to support the chest wall during respiration. By re-approximating the original rib locations the fractured ends of ribs are brought into proximity that facilitates and improves healing. It is also important to note that the coupling of the ribs to the connector bar is sufficiently compliant that the ribs naturally fall into a close approximation of their former position that accommodates rib cage motion and promotes healing while reducing pain. In essence the nearby intact ribs flexibly realigned flail sections of the chest and improve healing.

In most of these cases there is a traumatic chest injury so the additional risks posed by the additional wounds from the clamp system is very small and well tolerated.

BRIEF DESCRIPTION OF THE DRAWINGS

Throughout the several figures of the drawing identical reference numerals indicate identical structure, wherein.

DETAILED DESCRIPTION OF THE INVENTION

Figure 1:
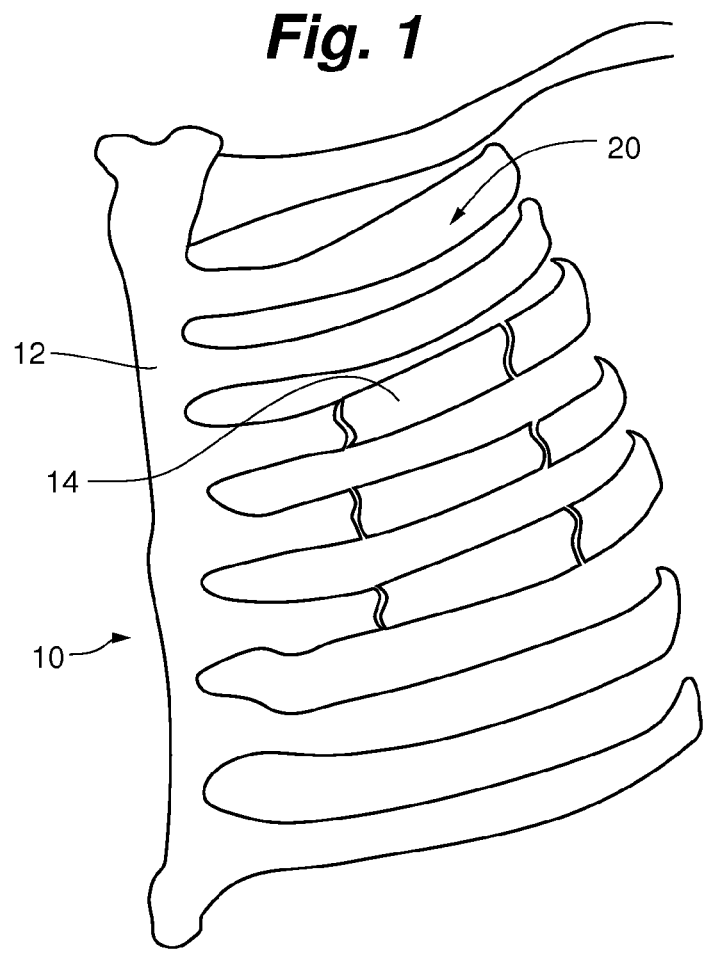
FIG. 1 is partial schematic view of a flailed chest.
Figure 2:
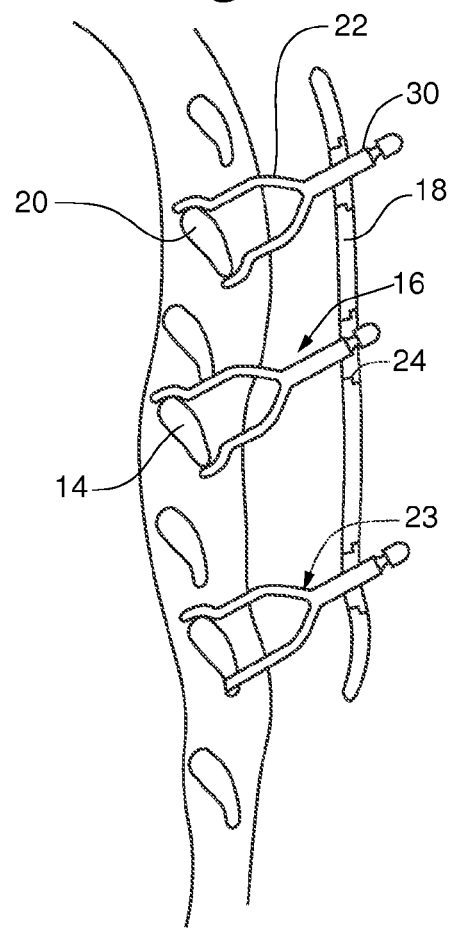
FIG. 2 is a cross section of a flail chest with the apparatus in place.
Figure 3:
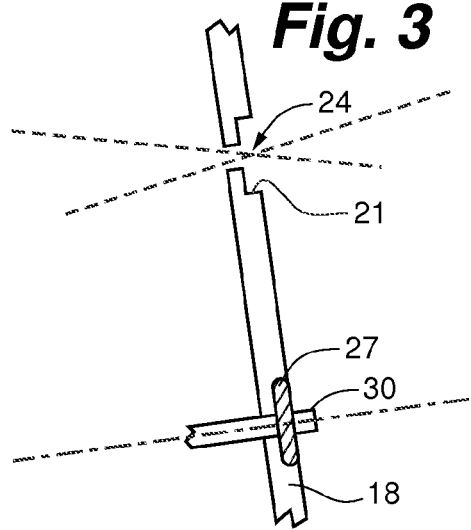
FIG. 3 is a cross section of the connector bar.

Turning to figures FIG. 1 through FIG. 3, FIG. 1 shows a partial frontal view of the chest area of a patient 10. The sternum 12 is seen along with several flail segments of the ribs. In the figure reference numeral 14 indicates a rib flail segment broken in at least two places. An intact rib is shown at 20.

FIG. 2 is a cross section of the chest showing flailed segments typified by segment 14 and also showing intact ribs typified in the figure by rib 20. In this sagittal view a set of three rib clamps are seen at reference numeral 23, 22 and 16. Rib clamp 16 is attached to rib flail segment 14 that has been pulled into alignment with is neighboring intact rib 20. Rib clamp 22 is connected to that rib and each clamp is in turn coupled to the connector bar 18. Note that in FIG. 2 that the clamps all orient approximately the same direction as they connect the rib segments. This facilitates the use of the connector bar 18.

FIG. 3 shows that each of the proximal pin segments of each rib clamp may be exteriorized and may protrude through apertures typified by aperture 24 in the connector bar. Each rib clamp is affixed to the connector bar 18 by an O-ring that sits in a groove 26 on each pin (see FIG. 4 and FIG. 5). The level of the various clamps is well controlled by the connector bar but the angular alignment is flexible to allow the individual ribs to seek their own optimal position. This resilient coupling improves patient outcomes. The O-ring is partially trapped by a lip 21 that engages the O-ring 27. The O-ring engagement gently forces the axis of the pin or cap to align with companion pins or caps dynamically to preserve chest geometry.

Turning to figures FIG. 4 through FIG. 11, FIG. 4 shows a typical rib clamp 16 in isolation. The rib clamp is an assembly including a first tine 36 and a second tine 32 with rib grasping distal tips. In this embodiment the first tine is integral with the proximal pin 30 structure. And the second tine 32 is free to pivot about joint pivot axis 34. The second tine carries a sector gear 70 seen best in FIG. 8 that engages a coarse thread screw 38 that will allow the tines to move together by rotation about joint 34 axis to grasp a rib 20. It is preferred to incorporate a socket into the screw 38 to accept an Allen wrench 80 or the like to adjust the screw 38 and advance or retract it to couple motion to the sector gear. Thumb screws on an extended screw are contemplated but Allen wrench or screwdriver adjustment is slightly preferred to reduce the overall profile of the device in use. Also seen in this view are the curved shaped segments 86 and 82 of the tines engaging a rib 20 seen in phantom view these curved shaped distal tips function to provide a rib grasping surface. The side view of FIG. 5 of the rib clamp in isolation shows the proximal rib clamp shank structure 30 clearly along the O-ring retainer groove 26.

Figure 6:
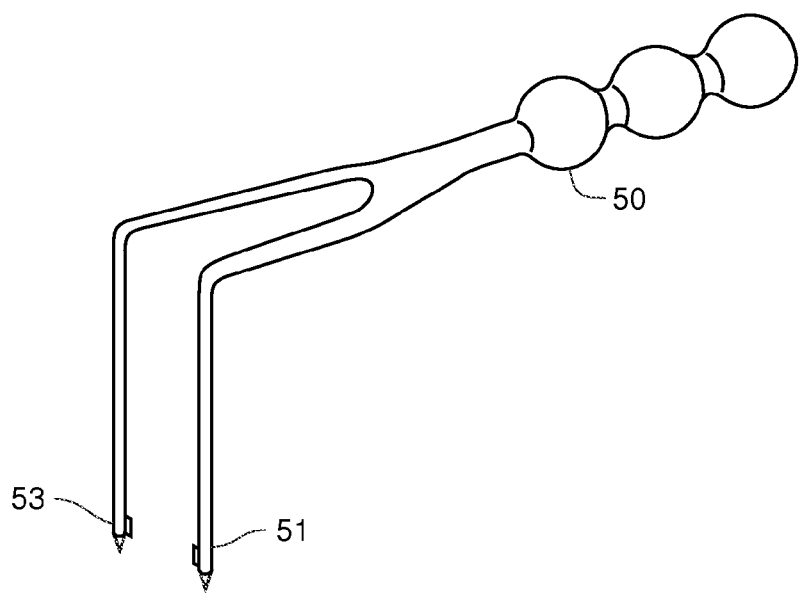
FIG. 6 is a perspective view of a companion tool to puncture the chest.

Placement of the rib clamps is facilitated by companion tool 50 show in FIG. 6. As is clear from the figure spaced tines 51 and 53 have reduced section zones and trocar like tips that pierce the skin and intercostal tissues when plunged into the chest. The two offset punctures will straddle the flail rib segment in use and permit the introduction of the rib clamp. This companion tool 50 can make the required wounds and engage the broken rib permitting retraction and positioning. Once the rib is successfully placed then the rib clamp may be inserted through the punctures and secure the rib. The use of the tool is optional as the physician make desire to make placement wounds using other surgical techniques.

Figure 7:
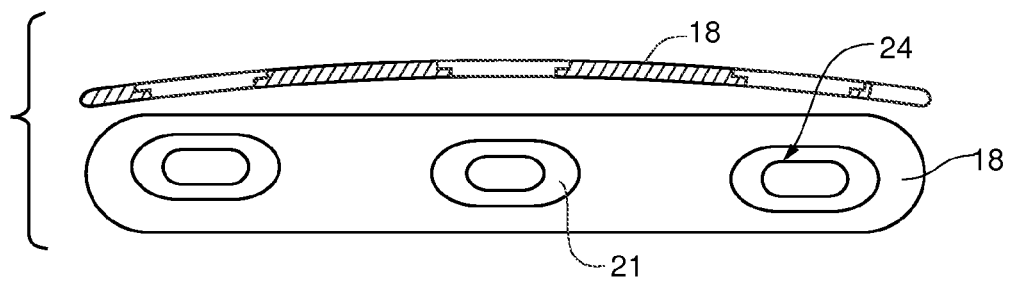
FIG. 7 is a composite view of the connector bar in cross-section and in plan view oriented to show structure.
Figure 8:
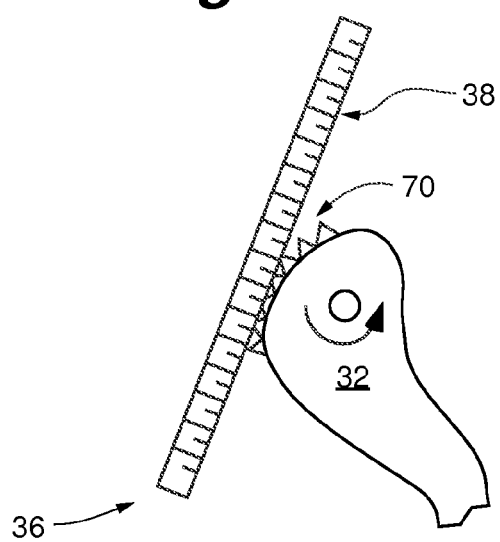
FIG. 8 is a partial view of a mechanism in isolation to adjust the rib clamps.
Figure 9:
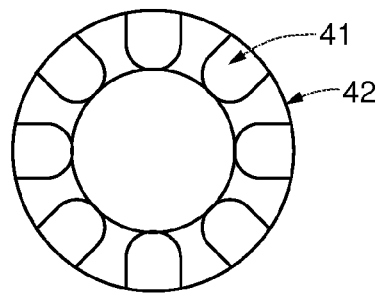
FIG. 9 is a cross section of the proximal segment of the rib clamp.

FIG. 7 shows a view of the connector bar 18 in isolation in a cross section view placed above a plan view and aligned to show the relative position of connector bar features. Several holes or apertures typified by hole 24 are provided along the length of the bar 18. Recessed lips typified by lip 21 allow the pin and groove 26 to protrude through the hole where the pin can be affixed by the application of an O-ring 27 forced on the pin and slide into groove 26 (see other figures).

Figure 4:
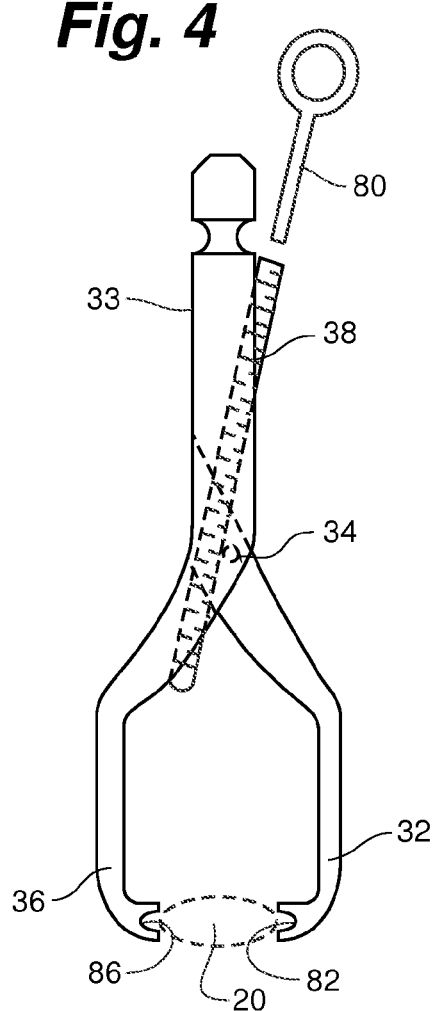
FIG. 4 is plan view of a rib clamp in isolation.
Figure 5:
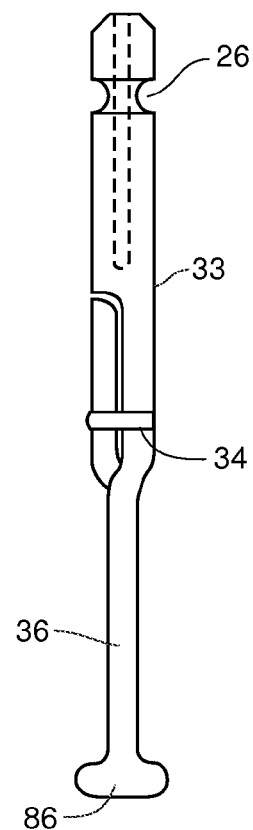
FIG. 5 is side view of a rib clamp in isolation.
Figure 10:
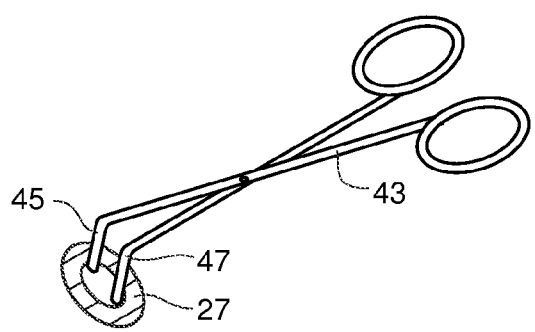
FIG. 10 is a perspective view of a companion tool to affix the o-rings to the rib clamps; and, FIG. 11 is a view of a rib clamp extension.

The tool of FIG. 10 may be used to position the O-rings onto or off of the proximal rib clamp shank typified by shank 33 (see FIG. 4). In general the o-ring is placed on the tool see FIG. 10 that expands the O-ring 27. Next the O-ring 27 and rolled off onto the pin cap 42 as better seen in FIG. 9 and FIG. 11. Optional grooves seen for example at reference numeral 41 in FIG. 9 may accept the O-ring pliers 43 tines 45 and 47 to assist in fixation of the O-ring 27 on the rib clamp cap 42.

Figure 11:
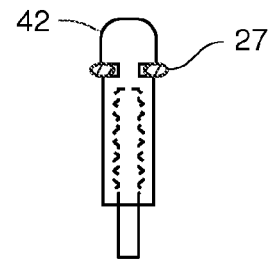

In most patients fixed pin length are usable especially for closely spaced ribs. However provision may be made for adjusting the length of a rib clamp by incorporating a screw cap pin 42 onto the clip as seen in FIG. 11. Here the cap is essentially a nut engaging a screw formed in the proximal rib clamp shank.

Many variations in structure can implement the present invention and the figures should be considered illustrative and not limiting.

What is claimed is:

1. A surgical system for treating a flail chest comprising:
one or more rib clamps for attachment to a segment of a rib;
each clamp having a terminal connector pin;
an elongate connector bar having multiple terminal pin reception holes, the holes defined by the elongate connector bar and extending therethrough;
each pin having an O-ring groove and an O-ring located in said groove to connect said pin to said connector bar;
whereby terminal pins connecting said rib clamps to said connector bar by said O-ring, function together to re-approximate and support the chest cavity to support respiration;
and wherein each of said rib clamps includes:
a first tine having a sector gear, and a rib grasping surface;
a second tine having a screw reception slot and a rib grasping surface; said first and second tines connected with a pivot joint to support rotation;
a screw connected to said first tine to engage said sector and force said grasping surfaces together.

* * * * *